United States Patent
Solomon

[11] Patent Number: 5,846,204
[45] Date of Patent: Dec. 8, 1998

[54] ROTATABLE ULTRASOUND IMAGING CATHETER

[75] Inventor: Rodney J. Solomon, Andover, Mass.

[73] Assignee: Hewlett-Packard Company, Palo Alto, Calif.

[21] Appl. No.: 886,880

[22] Filed: Jul. 2, 1997

[51] Int. Cl.[6] .................................................. A61B 8/12
[52] U.S. Cl. ........................................... 600/463; 600/585
[58] Field of Search .................................. 600/445–446, 600/462–463, 439

[56] References Cited

U.S. PATENT DOCUMENTS

| | | | |
|---|---|---|---|
| 5,024,234 | 6/1991 | Leary et al. | 128/663.01 |
| 5,085,221 | 2/1992 | Ingebrigtsen et al. | 600/446 |
| 5,176,142 | 1/1993 | Mason | 128/662.06 |
| 5,201,316 | 4/1993 | Pomeranz et al. | 128/662.06 |
| 5,203,338 | 4/1993 | Jang | 128/662.06 |
| 5,345,940 | 9/1994 | Seward et al. | 128/662.06 |
| 5,348,017 | 9/1994 | Thornton et al. | 128/662.06 |
| 5,368,035 | 11/1994 | Hamm et al. | 128/662.06 |
| 5,377,682 | 1/1995 | Uevo et al. | 600/446 |
| 5,413,107 | 5/1995 | Oakley et al. | 128/662.06 |
| 5,465,726 | 11/1995 | Dickinson et al. | 128/663.01 |
| 5,522,394 | 6/1996 | Zurbrugg | 128/662.06 |
| 5,570,693 | 11/1996 | Jang et al. | 600/463 |
| 5,592,942 | 1/1997 | Webler et al. | 600/446 |

FOREIGN PATENT DOCUMENTS

WO 89/04142  5/1989  WIPO .

Primary Examiner—Francis J. Jaworski

[57] ABSTRACT

An ultrasound catheter including a flexible, torsionally-rigid elongate transducer cable having proximal and distal ends, with a transducer housing fixably connected proximate to the distal end. An ultrasound transducer, having a substantially planar surface and a scan plane substantially perpendicular to the planar surface, is fixably connected to a first side of the transducer housing to provide a predetermined two-dimensional cross-sectional image corresponding to an angular position of the ultrasound transducer. The transducer generates a series of successive two-dimensional cross-sectional images. In one embodiment, the ultrasound transducer is a linear array transducer which produces a substantially rectangular scan plane. A guide wire sleeve which is fixably connected to a second side of the housing substantially opposing the first side, causes the transducer to follow a predetermined rotational path around the guide wire when a torque is applied to the proximal end of the transducer cable. The guide wire sleeve is preferably configured to insure that the planar surface of the ultrasound transducer is maintained in substantial parallel relationship with the guide wire positioned within the sleeve. An ultrasound imaging system comprising the ultrasound catheter also includes a positioning system coupled to the proximal end of the transducer cable. The positioning system applies a torque to the proximal end of the cable to rotate the array about an axis defined by the guide wire channel. A controller rotates the array between successive image scans and forms a three-dimensional image using the plurality of two-dimensional cross-sectional images generated by the array.

17 Claims, 2 Drawing Sheets

ROTATABLE ULTRASOUND IMAGING CATHETER

BACKGROUND OF THE INVENTION

1. Field of The Invention

The present invention relates generally to interventional catheters and, more particularly, to catheters providing ultrasound imaging.

2. Related Art

The use of ultrasound for medical imaging is well-known. Since its introduction, advances in technology and clinical practice have made ultrasound a leading medical diagnostic imaging modality. Ultrasound provides high-resolution real-time imaging without the use of ionizing radiation which is used in other imaging techniques. In addition, modern ultrasound equipment is relatively inexpensive and portable. This cost-effectiveness and portability has resulted in the widespread application of ultrasound imaging. For example, ultrasound is used in such clinical applications as cardiology, obstetrics and gynecology, general abdominal imaging and vascular imaging. In addition, ultrasound is commonly used in surgical and intravascular applications, as well as in guiding other interventional procedures.

A continuing objective of medical imaging techniques is to convey clinical information effectively. While traditional ultrasound image displays are extremely valuable, there has been an increasing interest in new methods for visualization of ultrasound data. There has been particular interest in visualizing the spacial relationships between successively acquired images, and the added clinical utility that such techniques offer. These include the increased information for diagnosis and treatment and for guiding other interventional procedures.

For example, therapeutic catheters are commonly used to perform electrophysiological procedures to diagnose and treat cardiac anatomical or conduction system abnormalities. Ultrasound is often used to provide imaging information of the therapeutic catheter's position. Typically, fluoroscopy is initially used to generally position an ultrasound imaging catheter and a separate therapeutic catheter in the left or right atrium or ventricle of the heart. Then, ultrasound imaging is used to assist in the control of a therapeutic device located near or at the end of the therapy catheter. However, conventional ultrasound catheters provide a narrow field of view, making it difficult to locate the therapeutic device. In addition, it is difficult to perform the diagnostic and therapeutic procedures while keeping the therapeutic device in the narrow field of view provided by the ultrasound catheter since both catheters have to be continually maneuvered throughout the performance of the procedure. The resulting unclear and inconsistent imaging makes it difficult to determine the position of the therapeutic device relative to the walls of the heart, resulting in uncertainty in the success of the procedure.

One conventional approach for determining the position of a therapeutic device in the ultrasound imaging window is described in U.S. Pat. No. 5,325,860 to Seward et al. Seward discloses a catheter having an ultrasound transducer and channel or port that runs axially along its length. A therapeutic device may be inserted through the treatment channel to deliver it to a position proximate to the distal end of the catheter for operation within the field of view provided by the transducer. A drawback to this approach is that it is difficult to maintain the cleanliness of the treatment channel. In addition, for the treatment channel to be sufficiently large to receive therapeutic devices, it must consume a significant portion of the catheter's internal volume. This requirement limits the space available for all other functional elements of the catheter, such as the ultrasound transducer. Thus, the size of the catheter must be increased to accommodate such other functional elements or conversely, the ultrasound transducer and other functional elements must be limited in size.

Another approach to aligning a therapeutic device within an ultrasound imaging window is described in U.S. Pat. No. 5,325,148 to Lesh et al. The Lesh device includes the use of a catheter with a tissue characterization assembly and an ablation assembly permanently fixed relative to each other in a single structure. A drawback to this approach is that the relative fixed positions of the ablative device and the ultrasound transducer are such that the therapeutic device is not in the field of view provided by the transducer. As a result, the transducer cannot be used to monitor the relative position of the therapeutic device and anatomical structure or tissue to receive the desired therapy. Therefore, this device is of little assistance during the performance of a diagnostic or therapeutic procedure.

In addition, a drawback to the above and other ultrasound catheters is that the therapeutic device is physically attached to the ultrasound catheter, limiting the relative movement of the catheters and restricting the location of the therapeutic device to the same general location that containing the ultrasound catheter. However, it may be necessary to view the therapeutic device from a location remote from the therapeutic catheter. For example, when performing intracardiac imaging and ablation therapy, it is often necessary to place the transducer in the right atrium/ventricle to view the ablation electrode in the left atrium/ventricle to reduce the risk of complications.

The inability of conventional ultrasound imaging techniques to continually provide information regarding the location of the therapeutic catheter has resulted in an attempt to generate 3-dimensional ultrasound images. One conventional approach to visualizing the spacial relationships between successively acquired images to obtain a 3-dimensional image has been to manually control of the transducer position. However, a manual positioning system has numerous limitations, proving to be an imprecise technique for positioning an ultrasound transmitting device. For example, with a manual system, the speed at which the array may be rotated is not readily controllable. In addition, an operator manually controlling the rotation of the array may induce stress on positioning system components as well as catheter components by abruptly changing the rotation speed and/or direction. Furthermore, a sufficiently abrupt change in rotational speed and/or direction could over-torque the aforementioned components leading to potentially serious damage to the catheter. In addition, with a manual positioning system the elasticity of the drive mechanism from the handle to the transducer may provide insufficient tactile feedback to the position control mechanism. As such, an operator may have difficulty correlating the extent of the manipulation of the position mechanism required for precise control of the transducer position.

What is needed, therefore, is a means for providing improved visualization of ultrasound data, including the spacial relationships between successively-acquired images. This will enable an administering sonographer to quickly and accurately obtain clinical information as well as to guide diagnostic and therapeutic procedures. Preferably, such a device should be capable of providing a three-dimensional field of view of the surrounding anatomical features to enable the clinician to perform a desired therapy with improved speed, accuracy and success.

SUMMARY OF THE INVENTION

The present invention overcomes the above and other drawbacks of conventional systems and techniques by providing a rotatable ultrasound imaging catheter and method for obtaining ultrasound imaging data utilizing the same. In one aspect of the present invention an ultrasound catheter is disclosed. The ultrasound catheter includes an elongate transducer cable having at its distal end an ultrasound transducer array and a guide wire channel adapted to enable the array to rotate about a guide wire. Significantly, application of a torque to a proximal end of the cable causes the array to travel a predetermined angular path around the guide wire to insonify a three-dimensional volume of a surrounding anatomical region. This enables the sonographer to accurately obtain clinical information for diagnosis and for guiding the performance of therapeutic procedures. In one embodiment of the invention the transducer array generates a series of two-dimensional ultrasound images of a surrounding anatomical region, each corresponding to an angular position of the array. In another embodiment, the transducer travels in a predetermined path around the guide wire to provide a plurality of successive two-dimensional images, each corresponding to an angular position of the transducer array.

The ultrasound transducer preferably has a substantially planar surface and generates a scan plane substantially perpendicular to that surface. The scan plane defines the two-dimensional cross-sectional images that correspond to each of the rotational positions of the transducer array. The guide wire sleeve is preferably configured to maintain the planar surface of the ultrasound transducer substantially parallel with a portion of the guide wire that is located within the guide wire channel. Accordingly, the guide wire within the guide wire channel defines an axis of rotation of the transducer array. Preferably, the guide wire sleeve is located relative to the array such that the guide wire channel is included within an extended plane that also includes the scan plane. In such an embodiment, the series of successive two-dimensional images converge, forming a contiguous insonified volume. Preferably, the elongate transducer cable is a torsionally rigid cable that is flexible in bending. This enables the array to be positioned in a predetermined angular location through the application of a torque to the proximal end of the cable. Preferably, the transducer housing is rigid to prevent unintended deflections of the array. Also, the transducer array is preferably a linear array which generates a scan plane which provides a substantially rectangular two-dimensional cross-sectional image.

In another aspect of the invention, an ultrasound imaging system is disclosed. The system includes an ultrasound catheter having a flexible, torsionally-rigid transducer cable. Secured adjacent to a distal end of the cable is a rotatable transducer array and a guide wire sleeve defining a guide wire channel. The guide wire channel is configured to enable the transducer array to travel in a predetermined path around a guide wire positioned within the channel. The system also includes a positioning system coupled to the proximal end of the transducer cable. The positioning system applies a torque to a proximal end of the cable to rotate the array about an axis defined by the guide wire channel. This enables the array to provide a plurality of two-dimensional cross-sectional images, each associated with an angular position of the array. A controller rotates the array between successive image scans and forms a three-dimensional image using the plurality of two-dimensional cross-sectional images generated by the array.

In one embodiment of this aspect of the invention, the system also includes a position feedback mechanism coupled to the array for providing the ultrasound imaging system with angular position data corresponding to each of the plurality of two-dimensional cross-sectional images. The controller periodically actuates the positioning system based upon the position feedback system to accurately rotate the array to various predetermined angular positions to obtain corresponding two-dimensional cross-sectional images.

In still another aspect of the invention a method for performing ultrasound imaging is disclosed. The method includes the steps of: (a) articulating a guide wire through a circulatory system to position a distal end of the guide wire at a desired location; (b) inserting a proximal end of the guide wire through a guide wire channel on a distal end of an elongate transducer cable having an ultrasound transducer proximate the distal end of said cable; (c) causing the transducer cable to travel over the guide wire to arrive at a location proximate the desired location; and (d) applying a torque to a distal end of the cable to cause the ultrasound transducer to rotate around the guide wire to obtain a plurality of two-dimensional cross-sectional images, each corresponding to an angular position of the ultrasound transducer, wherein one or more of the two-dimensional cross-sectional images include imaging the first desired location. Preferably, the method also includes a step (e) of processing the plurality of two-dimensional cross-sectional images to form a three-dimensional image. In one embodiment of the invention the method also includes the step of, before step (a) of inserting the therapeutic device at a first desired location within the subject.

Advantageously, the ultrasound catheter of the present invention provides a predetermined number of successive two-dimensional ultrasound images suitable for forming a three-dimensional ultrasound image of a desired anatomical region. Improved visualization of ultrasound data is thereby achieved, including the spacial relationships between successively-acquired images. Administering sonographers using the present invention may quickly and accurately obtain clinical information and guide diagnostic and therapeutic procedures with improved speed, accuracy and success.

Further features and advantages of the present invention, as well as the structure and operation of various embodiments of the present invention, are described in detail below with reference to the accompanying drawings. In the drawings, like reference numbers indicate like or functionally similar elements. Additionally, the left-most one or two digits of a reference numeral identifies the drawings in which the reference numeral first appears.

BRIEF DESCRIPTION OF THE DRAWINGS

This invention is pointed out with particularity in the appended claims. The above and further advantages of this invention may be better understood by referring to the following description when taken in conjunction with the accompanying drawings, in which:

DETAILED DESCRIPTION

Figure 1:
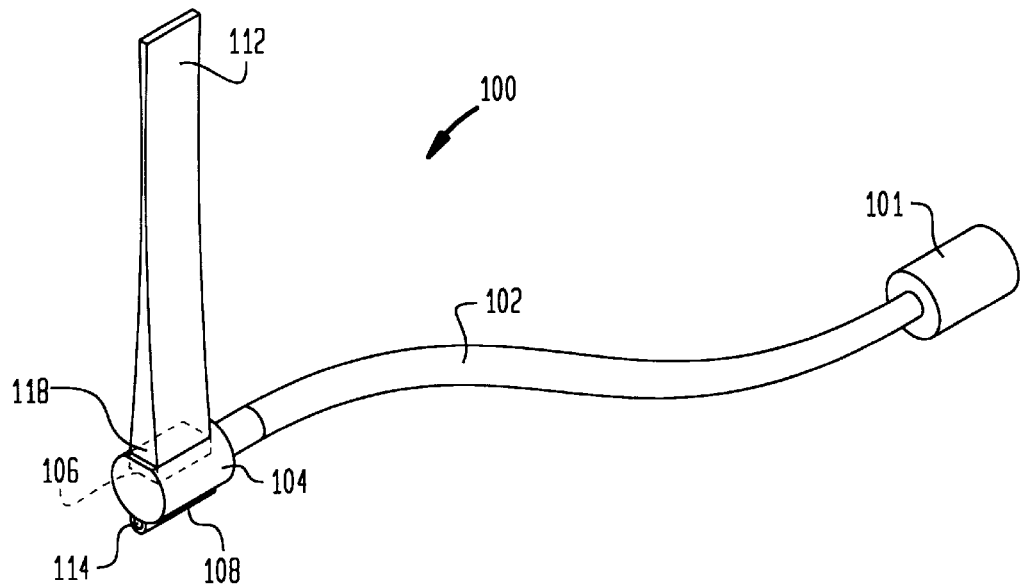
FIG. 1 is a perspective view of one embodiment of an ultrasound imaging catheter of the present invention.

A perspective view of one embodiment of the ultrasound imaging catheter 100 of the present invention is illustrated in FIG. 1. The catheter 100 has an elongate transducer cable 102 having a proximal end connected to a handle 101 and a distal end which houses a transducer array 106 and guide wire channel 114. The guide wire channel 114 is adapted to enable the array 106 to rotate about a guide wire (not shown). The transducer cable 102 is constructed to be torsionally-rigid cable which is also flexible in bending. A torque applied to the proximal end of the cable 102 causes the array 106 to travel along a predetermined angular path around the guide wire to insonify a three-dimensional volume of a surrounding anatomical region. This enables an administering sonographer to accurately obtain clinical information for diagnosis and for guiding the performance of therapeutic procedures.

Preferably, the array 106 is housed within a transducer housing 104 that is fixed proximate to the distal end of the transducer cable 102. The ultrasound transducer 106 includes an array of active elements and is fixably connected to a first side of the transducer housing 104. The guide wire channel 114 is preferably provided within a guide wire sleeve 108 that is fixably connected to or integral with the transducer housing 104. The guide wire channel 114 is adapted to enable the transducer array 106 to travel in a predetermined path around a guide wire having a diameter smaller than the diameter of the guide wire channel 114. This enables the array 106 to generate a plurality of successive two-dimensional images, each corresponding to an angular position of the transducer.

The ultrasound transducer array 106 preferably has a substantially planar surface 118 and generates a scan plane 112 substantially perpendicular to the surface 118. The scan plane 112 defines the two-dimensional cross-sectional images that correspond to each of the rotational positions of the transducer 106. In the illustrative embodiment shown in FIG. 1, the ultrasound transducer 106 comprises a plurality of elongated piezoelectric transducer elements arranged in a plane. The transducer array 106 produces the planar scan plane 112 which is substantially orthogonal to the planar surface 118 of the ultrasound transducer 106. In one embodiment, the ultrasound transducer 106 is a linear array producing an imaging plane 112 that has a substantially planar, rectangular shape. As is well-known in the art, linear array ultrasound transducers have such a rectangular field of view with the vertical borders of the field of view aligned with the edges of the transducer. In alternative embodiments, the ultrasound transducer 106 comprises a combination of one or more phased array, linear array or curved linear array elements, or some combination thereof, depending upon the desired application. Such arrays will produce imaging planes 112 having other well-known configurations. The array 106 is electrically connected to a flexible cable assembly (not shown) for providing image data to the remote ultrasound imaging electronics (discussed below).

As one skilled in the art would find apparent, the transducer cable 102 provides the necessary length to the ultrasound catheter 100 such that the transducer housing 104 can be positioned adjacent to a desired anatomical feature within a patient. As noted, the elongate transducer cable 102 is preferably a torsionally rigid cable that is flexible in bending. This enables the cable 102 to travel along any tortious path of the circulatory system, such as the great vessels of the heart, to position the array 106 to in a desired location. This construction also enables the array to be positioned in any predetermined angular position through the application of a torque to the proximal end of the cable 102, which remains outside the body of the patient at all times. This construction of the transducer cable 102 provides predetermined responses to an applied torque. As a result, the angular position of the array 106 can be controlled and faithfully represented.

In one embodiment, the transducer cable 104 has a three layered construction consisting of an inner flat ribbon coil, a middle braided wire tube and an external flexible elastomeric jacket. All three layers are in intimate contact with each other. The tubular braid is the primary torque transmission member. It will, however, if loaded in torsion, collapse inwardly and shorten. The inner flat ribbon cable is flexible in bending yet resistant to compression loads. Thus, the inner flat ribbon coil prevents the braid from collapsing when a torque is applied to the proximal end of the cable 102. The combination of the braid and coil is still not capable of transmitting torque with a minimum of deflection because it will foreshorten when torque is applied. The outer elastomeric jacket resists this foreshortening. Such a cable construction is considered to be well known in the art, and is commonly used in gastroscopes. In should be noted that cable 104 may have other constructions which result in a cable that is flexible in bending and rigid in torsion.

Preferably, the transducer housing 104 is rigid to prevent unintended deflections of the array 106 as it is rotated around the guide wire. This insures the ultrasound transducer 106 travels in a predetermined path around the guide wire located in the channel 114. Also, the guide wire sleeve 108 preferably configured to maintain the planar surface 118 of the ultrasound transducer 106 substantially parallel with a portion of the guide wire that is located within the guide wire channel 114. This prevents either end of the array 106 from inadvertently tilting towards and/or away from the guide wire.

Since the ultrasound transducer 106 travels in a predetermined path around the guide wire located in the channel 114, the guide wire defines an axis of rotation of the transducer array 106. In other words, the guide wire is used as an "axle" about which the ultrasound transducer 106 rotates. In a preferred embodiment of the invention, the guide wire sleeve 108 is located on a side of the transducer housing 104 which is substantially opposing the side on which the ultrasound transducer 106 is located. In such an embodiment, all or a portion of the scan plane 112 is included in a larger plane (not shown) that includes the guide wire sleeve 108. As a result, the series of successive two-dimensional images converge, forming a contiguous insonified volume. Accordingly, the rotation of the cable 102 causes the array 106 to assume a series of predetermined angular positions. At each of these positions a two-dimensional image is obtained, resulting in the insonification of a volume of the surrounding anatomical region. In the embodiment wherein the array 106 is a linear array, the two-dimensional images are substantially rectangular in shape and the resulting insonified volume is cylindrical.

As one skilled in the art would find apparent, in embodiments wherein the guide wire sleeve 114 is not on the opposite side of the housing 104, the resulting volume will not be cylindrical in shape since the successive two-dimensional images will not converge upon each other.

Figure 2:
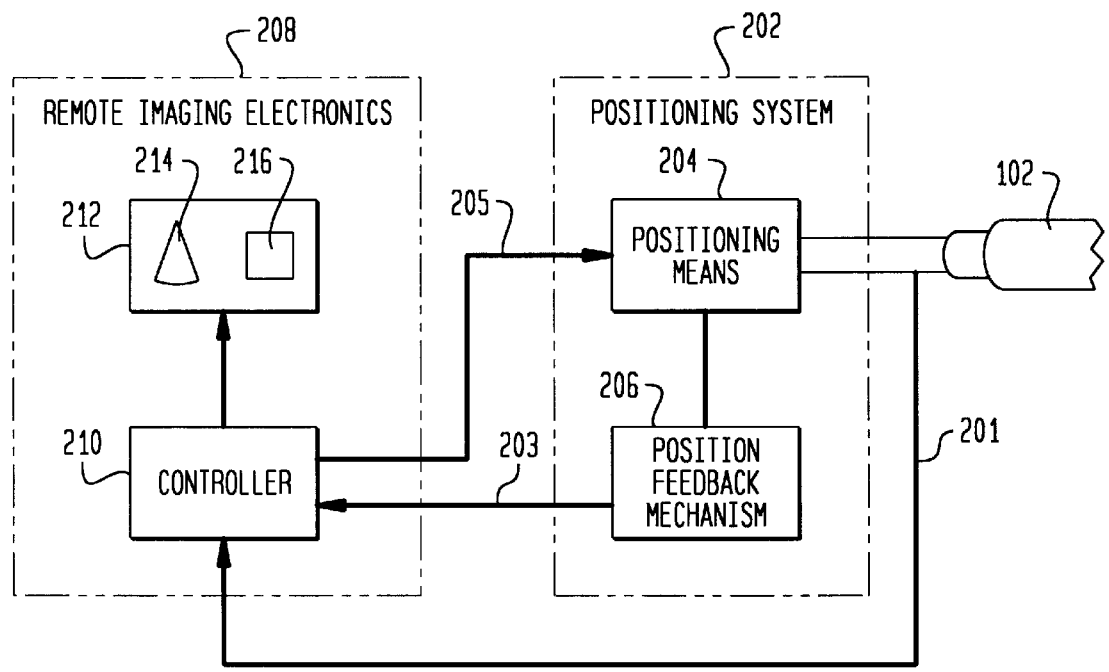
FIG. 2 is a functional block diagram of relevant portions of an ultrasound imaging system using the ultrasound imaging catheter of the present invention.

FIG. 2 is a functional block diagram of relevant portions of an ultrasound imaging system incorporating the ultrasound catheter 100. Generally, the system 200 includes a positioning system 202 coupled to the proximal end of the transducer cable 102. The positioning system 202 applies a torque to the proximal end of the cable 102 to rotate the array 106 about an axis defined by the guide wire channel 114. This enables the array 106 to provide a plurality of two-dimensional cross-sectional images, each associated with an angular position of the array 106. A controller 210 is coupled to the positioning means 204 via line 205 and controls the rotation of the array 106. The controller 210 rotates the array 106 between successive image scans and forms a three-dimensional image using the plurality of two-dimensional cross-sectional images generated by the array 106. It is understood that the system 200 includes a receiver/transmitter, scan converter and other elements not shown in FIG. 2.

In accordance with one embodiment of the present invention, the positioning system 202 is mechanically coupled to the cable 102. The positioning system 202 is capable of rotating the array 106 to various angular positions to obtain ultrasound imaging data along a plurality of corresponding scan planes 112. The array 106 is coupled to remote electronics 208 of the ultrasound imaging system 200, providing imaging data to the remote electronics 208 which produces a plurality of two-dimensional cross-sectional images corresponding to the scan planes 112.

The positioning system 202 employs a positioning means 204, such as an electrically powered motor, to apply a torque to the proximal end of the cable 102 to rotate the array 106. In the embodiment wherein the positioning means 204 is a motor, it is preferred that the motor is a direct current (DC) powered motor, such as a DC servo motor. Alternatively, the motor may be an alternating current (AC) powered motor or a stepper motor. Other well-known components necessary to implement such an arrangement are not shown in FIG. 2. For example, a gearbox may be necessary to be coupled to the motor for reducing the rotational speed of the motor. For each angular position, the array 106 provides image data corresponding to a two-dimensional cross-sectional image via line 201 to remote imaging electronics 208 described below.

In accordance with another feature of the present invention, the positioning system 202 comprises a position feedback mechanism 206 capable of providing the remote imaging electronics 208 with precise angular position data of the array 106 which corresponds to the scan plane 112 associated with a two-dimensional cross-sectional image. The position feedback mechanism 206 may comprise, for example, a digital or analog optical encoder. To provide precise angular position data of the array 106, the position feedback mechanism 206 is coupled to the cable 104 in a well-known manner such that rotation of the array causes the mechanism 206 to produce corresponding output signals to the remote imaging electronics 208 via line 203.

The position feedback mechanism 206 is coupled to the array 106, providing the remote electronics 208 with angular position data corresponding to each of the plurality of two-dimensional cross-sectional images. The controller 210 periodically actuates the positioning system 202 based upon the position feedback mechanism 206 to accurately rotate the array 106 to various predetermined angular positions to obtain corresponding two-dimensional cross-sectional images.

The position feedback mechanism 206 output may be transformed into an angular position of the array 106 and displayed on a CRT display 212 in the remote imaging electronics 208. The position feedback signal 203 is sent to the controller 210 located in the remote imaging electronics 208 which transforms the signal to an angular position corresponding to an array orientation by employing appropriate well-known electronics and software. The angular position is sent to the CRT display 212 and displayed on an angular position display window 214 which is located adjacent to a main two-dimensional image window 216. In a preferred embodiment, the position feedback mechanism and other components of the system 200 may be configured as described in U.S. Pat. No. 5,181,514 to Solomon et al., assigned to the assignee of the present invention, and incorporated herein by reference in its entirety.

Further, the position feedback mechanism 206 is coupled to the controller 210 via line 203, providing precise angular position data (which corresponds to the scan plane orientation) as the array is rotated through a plurality of scan planes. Preferably, the controller 210 correlates the array position data with the power provided to actuate the positioning means 204 such that the array 106 is rotated to obtain image data at regularly incremented angular positions. In one embodiment, the controller 210 controls the positioning system 202 and generates images on CRT 212 in a manner which is synchronized with the subject's ECG cycle. Such an approach is described in U.S. Pat. No. 5,181,514 to Solomon et al.

Figure 3:
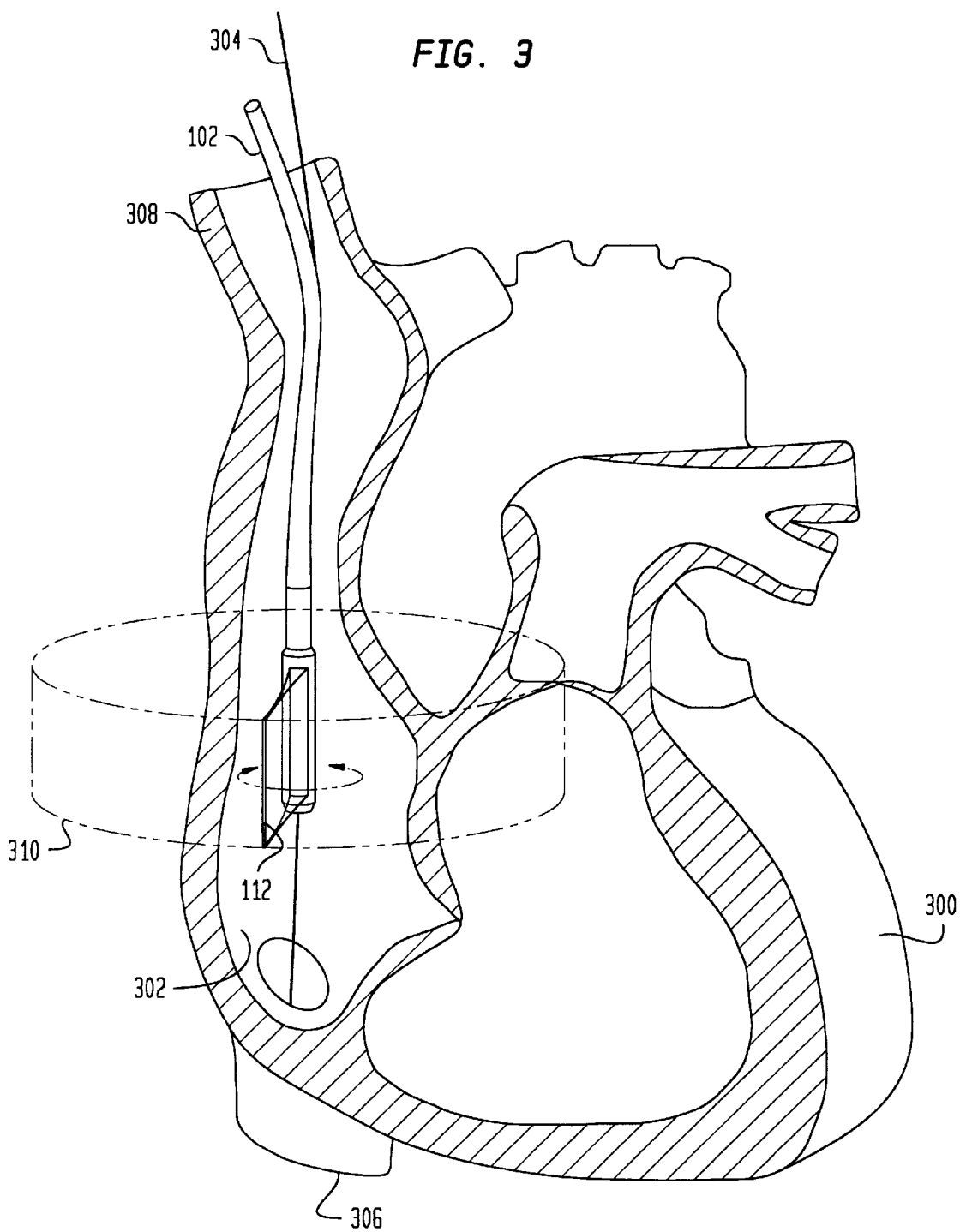
FIG. 3 is a cross-sectional view of a human heart with the catheter of the present invention inserted along a guide wire.

FIG. 3 shows a cross-sectional view of a human heart with one embodiment of the ultrasound imaging catheter 100 of the present invention positioned within the atrium of the heart. As shown, a guide wire 304 extends through the superior vena cava 308 to the inferior vena cava 306. The guide wire 304 is positioned in the illustrated position using procedures well known in the art. With the guide wire channel 114, the transducer housing 104 travels along the guide wire 304 to be positioned within the right atrium such that the region of interest is within the interrogated volume. As shown, the transducer cable 102 is flexible in bending and generally follows the path of the guide wire 304.

The scan plane 112 of the array 106 is rotated around the guide wire 304 to successive predetermined angular positions. At each of these positions a two-dimensional ultrasound image is obtained and provided an ultrasound imaging system such as the system 200 described above. The sequential images are formed into a composite three-dimensional image defining the interrogation volume 310. As shown in FIG. 3, the interrogation volume 310 is cylindrical due to the rectangular shape of the scan plane 112 and the relative location of the array 106 and the sleeve 108. When the array 106 is rotated completely around the guide wire 304, a cylindrical volume is interrogated as shown in FIG. 3. However, as one skilled in the art would find apparent, any predetermined number of successive two-dimensional ultrasound images may be obtained to form any desired interrogation volume to view a desired anatomical region.

In operation, a method for performing ultrasound imaging includes articulating the guide wire 304 through a circulatory system to position a distal end of the guide wire at a desired location. In the application shown in FIG. 3, this would be somewhere in the inferior vena cava 306. Then, the proximal end of the guide wire 304 is inserted through the guide wire channel 114 on the distal end of the elongate transducer cable 102. The transducer cable 102 is then fed into the patient in a known manner to travel over the guide wire 314 and arrive at a desired location. A torque is then applied to the distal end of the cable 102, causing the array 106 to rotate around the guide wire 314. Successive image scans are taken to obtain a plurality of two-dimensional cross-sectional images, each corresponding to an angular position of the ultrasound transducer 106. The images are provided to the controller 210 which processes the plurality of two-dimensional cross-sectional images to form a three-dimensional image. This methodology may be used in conjunction with diagnostic or therapeutic procedures. This enables the administering sonographer to quickly and accurately obtain clinical information or to guide diagnostic and therapeutic procedures.

While various embodiments of the present invention have been described above, it should be understood that they have been presented by way of example only, and not limitation. Thus, the breadth and scope of the present invention are not limited by any of the above-described exemplary embodiments, but are defined only in accordance with the following claims and their equivalents.

What is claimed is:

1. An ultrasound catheter comprising an elongate transducer cable having at its distal end an ultrasound transducer array and a guide wire channel defining an axis of rotation of said transducer array, wherein a guide wire inserted into said channel serves as an axle about which said transducer array rotates, wherein said array rotates about the guide wire in response to a rotational force applied to a proximal end of said transducer cable to insonify a plurality of successive two-dimensional images suitable for forming a three-dimensional image.

2. The ultrasound catheter of claim 1, wherein said array generates a series of two-dimensional ultrasound images of a surrounding anatomical region, each of the images corresponding to an angular position of said array relative to said guide wire.

3. The ultrasound catheter of claim 1, wherein said ultrasound transducer has a substantially planar surface and generates a scan plane substantially perpendicular to said surface, said scan plane defining said two-dimensional images.

4. The ultrasound catheter of claim 3, wherein said guide wire sleeve is configured to maintain said planar surface of said ultrasound transducer substantially parallel with a portion of said guide wire located within said guide wire sleeve.

5. The ultrasound catheter of claim 4, wherein said guide wire sleeve has a length sufficient to insure said planar surface of said ultrasound transducer is maintained in substantial parallel relationship with said guide wire channel.

6. The ultrasound catheter of claim 3, wherein an extended plane including said scan plane includes said axis of rotation.

7. The ultrasound catheter of claim 1, wherein said elongate transducer cable is a flexible, torsionally rigid cable.

8. The ultrasound catheter of claim 1, wherein said transducer housing is rigid.

9. The ultrasound catheter of claim 1, wherein said guide wire sleeve is located on a second side of said transducer housing opposing said first side of said transducer housing.

10. The ultrasound catheter of claim 1, wherein said ultrasound transducer is a linear array ultrasound transducer that generates a scan plane which provides a substantially rectangular two-dimensional cross-sectional image.

11. The ultrasound catheter of claim 1, wherein said ultrasound transducer is a linear array transducer.

12. An ultrasound imaging system comprising:

an ultrasound catheter having secured adjacent to a distal end of a flexible, torsionally-rigid transducer cable a rotatable transducer array and a guide wire sleeve having a guide wire channel defining an axis of rotation of said transducer array, and configured to enable said transducer array to travel in a predetermined path around an axle formed by a guide wire within said channel;

a positioning system for applying a torque to a proximal end of said transducer cable to rotate said array about an axis defined by said guide wire channel to provide a plurality of two-dimensional cross-sectional images; and a controller for forming a three-dimensional image from said plurality of two-dimensional cross-sectional images.

13. The system of claim 12, further comprising:

a position feedback mechanism coupled to said array for providing said controller with angular position data corresponding to each of said plurality of two-dimensional cross-sectional images.

14. The system of claim 12, wherein said controller is synchronized to a particular time in a subject's electrocardiogram cycle and coupled to said positioning system, wherein said controller periodically actuates said positioning system to rotate said array to various orientations which provide said plurality of corresponding two-dimensional cross-sectional images at the particular time in the subject's electrocardiogram cycle for providing a three-dimensional image associated with that particular time.

15. A method for performing ultrasound imaging, comprising the steps of:

(a) articulating a guide wire through a circulatory system to position a distal end of the guide wire at a desired location;

(b) inserting a proximal end of said guide wire through a guide wire channel on a distal end of an elongate transducer cable having an ultrasound transducer proximate said distal end of said cable;

(c) causing said transducer cable to travel over said guide wire to arrive at a location proximate said desired location; and (d) applying a torque to a distal end of said cable to cause said ultrasound transducer to rotate about an axis of rotation defined by the guide wire to obtain a plurality of two-dimensional cross-sectional images, each corresponding to an angular position of said ultrasound transducer, wherein the guide wire serves as an axle about which said transducer rotates when said guide wire is positioned within said guide wire channel.

16. The method of claim 15, further comprising the step of:

(e) processing said plurality of two-dimensional cross-sectional images to form a three-dimensional image.

17. The method of claim 16, further comprising the step of:

(f) before said step (a), inserting a therapeutic device at a first desired location in the subject.

* * * * *